(12) United States Patent
Schulat et al.

(10) Patent No.: US 8,394,637 B2
(45) Date of Patent: Mar. 12, 2013

(54) HANDHELD ANALYZER FOR TESTING A SAMPLE

(75) Inventors: Jochen Schulat, Mannheim (DE); Gertrud Albrecht, Mannheim (DE); Bernhard Kern, Heidelberg (DE)

(73) Assignee: Roche Diagnostics Operations, Inc., Indianapolis, TN (US)

( * ) Notice: Subject to any disclaimer, the term of this patent is extended or adjusted under 35 U.S.C. 154(b) by 1100 days.

(21) Appl. No.: 12/131,366

(22) Filed: Jun. 2, 2008

(65) Prior Publication Data
US 2009/0298182 A1    Dec. 3, 2009

(51) Int. Cl.
*G01N 35/02*    (2006.01)

(52) U.S. Cl. ............ 436/50; 422/50; 422/501; 422/502; 436/180; 436/44; 436/48; 436/171; 700/266; 700/302

(58) Field of Classification Search .................... 422/58, 422/61, 63, 104, 50, 501–502; 436/44, 811, 436/808, 68, 95, 150, 48, 46, 171, 180, 50; 700/266, 302; 204/403.02, 403.01, 407; 600/583; 221/66
See application file for complete search history.

(56) References Cited

U.S. PATENT DOCUMENTS

| | | | | |
|---|---|---|---|---|
| 4,937,050 A * | 6/1990 | Meinecke et al. | ........... | 422/68.1 |
| 5,438,271 A * | 8/1995 | White et al. | .................. | 324/444 |
| 5,660,791 A * | 8/1997 | Brenneman et al. | ............ | 422/58 |
| 6,821,483 B2 * | 11/2004 | Phillips et al. | .................. | 422/58 |
| 6,827,899 B2 * | 12/2004 | Maisey et al. | ................... | 422/61 |
| 2003/0039584 A1 * | 2/2003 | Schabbach et al. | ............. | 422/64 |
| 2003/0191415 A1 | 10/2003 | Moerman et al. | | |
| 2005/0042765 A1 | 2/2005 | Hubner et al. | | |
| 2005/0187444 A1 | 8/2005 | Hubner et al. | | |
| 2006/0240568 A1 * | 10/2006 | Petruno et al. | ................ | 436/514 |
| 2007/0009381 A1 | 1/2007 | Schulat et al. | | |
| 2007/0183925 A1 | 8/2007 | Schabbach | | |

FOREIGN PATENT DOCUMENTS

| | | |
|---|---|---|
| CA | 2511179 A1 | 7/2004 |
| EP | 0779983 B1 | 11/1999 |
| EP | 1022565 B1 | 7/2000 |
| EP | 1508807 A2 | 2/2005 |
| EP | 1574855 A1 | 9/2005 |
| EP | 1 995 594 B1 | 5/2007 |
| JP | 4604109 | 10/2010 |
| WO | 2004/057345 A2 | 7/2004 |
| WO | 2005/065828 A1 | 7/2005 |
| WO | 2005/085840 A1 | 9/2005 |

* cited by examiner

*Primary Examiner* — Jyoti Nagpaul
(74) *Attorney, Agent, or Firm* — Krieg DeVault LLP

(57) ABSTRACT

The invention relates to a handheld analyzer for testing a sample, in particular of a biological fluid, for a medically significant component. It comprises a test unit, which detects the correct positioning of an analytical consumable means in a conveyance pathway. According to this invention, the test unit has both an electric switch component which mechanically senses the positioning of the analytical consumable means and an optical sensor unit which optically senses the positioning of the analytical consumable means on the conveyance pathway. The handheld analyzer is controlled as a function of a comparison of the signals of the electric switch component and the optical sensor unit. It is possible in this way to reduce malfunctions or operating errors associated therewith.

20 Claims, 4 Drawing Sheets

HANDHELD ANALYZER FOR TESTING A SAMPLE

TECHNICAL FIELD OF THE INVENTION

The present application relates to a handheld analyzer for testing a sample, and more particularly to a handheld analyzer for testing a biological fluid for a medically significant component, and a method relating to operating same.

BACKGROUND

For chemical and biochemical analysis of solid and liquid sample materials, carrier-bound rapid tests have become established in specialized laboratories and in particular also for use out of stationary laboratories. Such carrier-bound rapid tests are based on a specially developed dry chemistry and can be performed easily and in an uncomplicated manner even by a layperson despite the often complex reaction involving sensitive reagents.

Test elements for determining the blood glucose level of diabetics are a familiar example of carrier-bound rapid tests. Diagnostic test elements designed in strips are also referred to as test strips. Known embodiments include for example single-field or multi-field test strips for urinalysis and various indicator papers. In addition to test elements in strip form, other forms of carrier-bound tests also exist, so we speak in more general terms of analytical consumable means. Analytical consumable means can also generally refer to lancet or sample withdrawal elements, not just testing elements.

Such analytical consumable means can be used with a handheld analyzer which analyzes a color change of a test strip, e.g. photometrically by using an optical analysis device. In some systems, analytical consumable means are stored in a rotary drum magazine, such as that described in EP 1 022 565, for example, the disclosure of which is hereby incorporated by reference herein in its entirety. A rotary drum magazine can have several chambers which are, for example, arranged in a ring and may contain the analytical consumable means. Typically, each chamber has an insertion opening and a withdrawal opening on opposite front ends of the rotary drum magazine. These openings are each closed with a sealing film to protect the analytical consumable means from harmful environmental influences such as light, humidity or dust.

With known handheld analyzers such as the "Accu-Chek® Compact Blood Glucose Meter" from Roche Diagnostics GmbH, a check is performed by actuation of a withdrawal device to determine whether an analytical consumable means is still present in a chamber of the rotary drum magazine or whether it has already been withdrawn. The known handheld analyzer has two electric test circuits. A first test circuit is closed by a dog mounted on a push rod of the withdrawal device when this push rod is inserted into a chamber of the rotary drum magazine. If a consumable means is in the chamber, it is ejected by the push rod, and in doing so, a switch is activated by the consumable means, thereby closing a second test circuit. If operation of the withdrawal device results in closing the first test circuit only but not in closing the second test circuit, this means that the respective chamber of the rotary drum magazine is empty.

Other exemplary systems with test element positioning and/or detection means are disclosed in EP 0 779 983 and EP 1 508 807, the disclosures of which are hereby incorporated herein by reference in their entireties.

Handheld analyzers for testing a medically significant component of a sample, such as devices for determining the blood glucose level, are often used by people whose perception or manual dexterity is impaired due to age or illness. It is therefore important for such analyzers to be as easy to handle as possible and that operating errors or malfunctions are ruled out as much as possible.

The object of the invention is to provide a handheld analyzer for testing a medically significant component of a sample and a method for operating such a handheld analyzer that reduces malfunctions or operating errors associated therewith.

SUMMARY

This object and others that will be appreciated by a person of ordinary skill in the art are achieved according to the embodiments of the present invention disclosed herein. In one embodiment, the present invention comprises a handheld analyzer comprising an analysis device, a display device, and a housing, which may include a loading opening for receiving a replaceable magazine that may contain analytical consumable means, in particular test strips. The magazine may have several chambers and may be designed as a rotary drum magazine, for example, wherein the chambers each have an opening on an end face of the magazine, which openings can be sealed each with a sealing film. Furthermore, the handheld analyzer comprises a withdrawal device for withdrawing one of the analytical consumable means from the magazine by means of which one of the consumable means may be conveyed out of a the chamber of the magazine and onto a conveyance pathway. During the process or subsequently, the analytical consumable means is conveyed on the conveyance pathway to the analysis sensor of the analysis unit for an analysis to be performed there. A test unit determines the correct positioning of an analytical consumable means on the conveyance pathway.

A handheld analyzer according to the invention thus has the particular feature that it comprises a test unit which detects the correct positioning of an analytical consumable means in the conveyance pathway, wherein the test unit comprises an electric switch component that mechanically senses the positioning of an analytical consumable means on the conveyance pathway, assumes at least one switch position, which represents the presence of an analytical consumable means and delivers a switch signal as a function of the positioning of the analytical, consumable means, as well as an optical sensor unit which optically senses the positioning of an analytical consumable means on the conveyance pathway and delivers a sensor signal as a function of the positioning of the analytical consumable means, and a control unit which analyzes the switch signal of the electric switch component and analyzes the sensor signal of the optical sensor unit and controls the handheld analyzer as a function of a comparison of these signals.

With the handheld analyzer according to the invention, a test unit is provided which determines a correct positioning of an analytical consumable means in the conveyance pathway. Positioning of a consumable means in the conveyance pathway is understood to refer to a situation in which the withdrawal device has withdrawn a consumable means from the magazine and conveyed the consumable means onto the conveyance pathway so that, if the withdrawal from the magazine has been performed successfully, i.e., without any error, a consumable means is situated in the conveyance pathway, i.e., is positioned in the conveyance pathway. The term "correct positioning" is understood to refer to the fact that the consumable means is actually in a position predetermined by the process sequence. In such a predetermined position, e.g. the mere presence of the consumable means is ascertained, i.e., a check is performed to determine whether it is present in the conveyance pathway and is positioned correctly inasmuch as it is present at the intended location or in the intended area. In other cases, an exact position test of the consumable means may be performed, wherein it is ascertained whether the consumable means is in an exact location or position on the conveyance pathway. The check of the correct positioning of the consumable means may in these cases relate to any position of the consumable means in the conveyance pathway. In some embodiments, the check of the correct positioning of the consumable means may be performed in the position in which the analysis is performed with the analysis sensor. In other embodiments, however, it may be advantageous to check the correct positioning of the consumable means in a position other than this measurement position, in particular in a position which is attained by the consumable means before it reaches the measurement position.

The test unit comprises an electric switch component and additionally an optical sensor unit which independently and jointly sense the positioning of the analytical consumable means on the conveyance pathway and deliver a switch signal and a sensor signal, respectively, according to the sensed positioning, these signals being analyzed jointly by a control unit to ascertain whether a verification and/or check of one signal is possible on the basis of the other signal. This makes it possible to check for faults or malfunctions, in particular in the electric switch components which occur in particular due to swelling of the electric contacts, and to do so in a purposive manner and thereby limit any resulting damage.

For example, it is possible due to the inventive design of the handheld analyzer to ensure that malfunctions due to soiled electric contacts of the electric switch component are greatly reduced. Such soiling occurs especially in mobile use of the handheld analyzers to a particular extent because these devices are used and/or stored by users in a wide variety of situations and especially in less suitable environments which are characterized by moisture and soiling in particular. The risk of soiling of the contacts occurs in particular due to the fact that the housing of the handheld analyzer has openings, in particular for supplying or removing the analytical consumable means through which dust and other dirt particles can penetrate into the housing and may be deposited on the contacts of the electric switch component and can influence the electric switch performance. There may also be negative effects on the mechanical functionality of the electric switch component.

For example, this may lead to malfunctions, which are referred to as a continuous strip pile-up or a strip jam. With the continuous strip pile-up, the electric contact which is prevented due to soiling is interpreted by the control unit as absence of the consumable means so that with the help of the withdrawal device, a new consumable means is withdrawn from the magazine and conveyed onto the conveyance pathway until it reaches the area of the electric switch means. This is repeated either until the magazine is completely empty (continuous strip pile-up) or until the consumable means have been advanced over one another and have blocked in the conveyance pathway (strip jam), thereby precluding functionality of the handheld analyzer. Precisely these malfunctions described here, which are very annoying for the user and are also expensive due to the unnecessary consumption of consumable means, can be reduced significantly according to the present invention.

The inventive implementation of the handheld analyzer with the inventive test unit which allows verification and/or checking of the switch signal of the electric switch component on the basis of the optical sensor signal of the optical sensor unit enables checking of the electric switch signal by the optical sensor unit, in particular with the verified result that no consumable means is present in the conveyance pathway. If the presence of the consumable means and/or its correct positioning is/are detected and/or determined by the optical sensor unit contrary to the incorrect signal of the defective electric switch component, then the control unit will prevent further continuous withdrawal of consumable means from the magazine by the withdrawal device, so that the aforementioned malfunctions are largely prevented.

Due to the inventive design of the test unit with an electric switch component which ascertains a correct positioning of an analytical consumable means on the basis of a mechanical sensing operation, and an optical sensor unit, which determines a correct positioning on the basis of an optical sensing, a very universal and reliable verification by the test unit of the correct positioning is made possible.

In one embodiment, the electric switch component is designed so that it contains a displaceable switch element which is implemented, e.g., as a spring-loaded, displaceable peg and is used to mechanically sense the surface of the consumable means, which is typically designed in the form of a strip or as an essentially square piece and to close or open an electric contact based on a displacement of the switch element as a result of the sensing operation. Due to the mechanical sensing of the surface of the consumable means, it is possible very reliably and in a robust manner to obtain information about the positioning of the consumable means in the area of the electric switch component. This electric switch component in particular has proven to be less susceptible to deformation of the consumable means or vibration of the handheld analyzer.

Through the inventive combination of the robust and less susceptible electric switch component for detecting correct positioning with the optical sensor unit which detects the correct positioning of the consumable means on the basis of an optical detection, the reliability of the information provided by the test unit regarding the correct positioning is significantly increased. The optical sensor unit here is implemented either as a passive optical sensor unit or as an active optical sensor unit. The passive optical sensor unit comprises exclusively an optical receiver which detects characteristic optical properties of the consumable means in the sensor area of the optical sensor unit which sensor area is situated in the conveyance pathway. Active optical sensor units are characterized by active illumination of the sensor area so that active optical sensor units generate a reliable sensor signal even under difficult circumstances.

Especially in the case of soiling on the consumable means, active optical sensor units exhibit a significantly improved signal quality. The optical sensor unit is preferably used in reflective operation so that the active illumination of the sensor area is on the same side of the conveyance pathway as the optical receiver which detects the radiation reflected by the consumable means. This permits a very compact design of the optical sensor unit. As an alternative to this, the transmitting design of the optical sensor unit has proven successful with which the individual components are arranged on the two sides of the conveyance pathway and/or the consumable means and are thus arranged opposite one another. This allows a separate design of the individual components of the optical sensor unit, each of which requires a smaller design space with an increased cabling complexity, and is therefore especially advantageous for installation in a very small handheld analyzer.

In embodiments in which the electric switch component comprises a displaceable peg-shaped switch element which has an end tapering conically in the direction of the consumable means and facing the analytical consumable means, it is possible to detect not only the presence and/or the positioning of the analytical consumable means in the area of the switch element but additionally the consumable means can be actively positioned by the fact that the peg with its conically tapering end engages in an elevation and/or recess in the consumable means, so that the consumable means is displaced into a desired analysis position and/or held there. The term "recess" is also understood to include an opening or a hole in the consumable means. To support this positioning function, the displaceable peg is preferably spring-mounted so that the spring action works on the consumable means, moving it into the desired position for analysis.

This combined function of the test unit on the one hand as a double unit and thus a unit for verification and/or checking for determination of the correct positioning of the analytical consumable means and on the other hand as a unit for active positioning in the desired position for analysis provides a very reliable and not very susceptible implementation of a handheld analyzer which is therefore highly error tolerant. This position assumed due to the positioning for the potential analysis is an optimal position for optical detection of the correct positioning of the consumable means, which allows very reliable operation of the handheld analyzer. The electric switch component may be designed so that its test function and its positioning function relate to the same or different positions of the analytical consumable means in the conveyance pathway.

In the disclosed embodiments of the handheld analyzer with an electric switch component, which cooperates with a position-specific surface design of the analytical consumable means and implements different switch states as a function of the position of the displaceable switch element, it is possible to allow a highly differentiated switching behavior of the test unit. This position-specific surface design is implemented by a contour which is characterized in particular by a channel on the analytical consumable means that varies in width and/or depth, and by a ramp on the analytical consumable means that varies in width and/or height. Due to the penetration of the switch element into the position-differentiating channel and/or the lifting up due to the position-differentiating ramp, it is possible to selectively detect different positions of the consumable means and to control the handheld analyzer by means of the control unit in a manner that is differentiated with regard to position. In particular, it is possible to optimally control the point in time of the analysis. Especially with regard to a mode of operation that is efficient with regard to consumption, this proves to be especially advantageous because the individual electric components of the handheld analyzer can be activated and/or deactivated at an early point in time in a purposive manner to minimize the electric energy consumption. In this way it is possible to reduce the frequency of malfunctions.

In one embodiment of the handheld analyzer, the optical sensor unit is designed so that it detects the position of a switch element of the electric switch component, e.g., of a displaceable peg itself and thus provides the possibility for setting the electric switch signal of the electric switch component in relation to the position of the switch element, which depends on the positioning of the analytical consumable means in the conveyance pathway and thereby allowing a verification and/or check on the positioning signal of the electric switch component by means of the optical sensor unit. This embodiment of the test unit allows a very compact design which provides a modularity of the test unit in the handheld analyzer. The good possibility for integration of the test unit thereby achieved also provides an implementation of the inventive handheld analyzer that is easy to repair.

According to another embodiment of the handheld analyzer, the optical sensor unit for detecting the positioning of the analytical consumable means on the conveyance pathway and the analysis sensor are integrated into a joint sensor unit. Integration here may mean that both sensors are combined in one structural unit or it means that both sensors are implemented in a single sensor which fulfills both functions. Especially in the design of both sensors in the form of optical sensors, it is possible to implement both functionalities jointly with a single sensor. In this case, the two functionalities are implemented in chronological succession, first the functionality of the optical sensor unit for detecting the positioning of the analytical consumable means on the conveyance pathway and then the functionality of the optical analysis sensor for the optical analysis of the sample. This inventive handheld analyzer shows, in addition to a reduction in malfunctions, a very compact design which especially facilitates the manageability of the handheld analyzer. In addition, due to the reduction in the number of sensors, an improvement in reliability and thus an additional reduction in the number of malfunctions are possible.

According to yet another embodiment of the handheld analyzer, withdrawal of an analytical consumable means from the magazine by the withdrawal device is prevented by means of the control unit if either the switch signal of the electric switch component or the sensor signal of the optical sensor unit represents correct positioning of an analytical consumable means on the conveyance pathway and the respective other signal represents incorrect positioning of an analytical consumable means on the conveyance pathway and thus there are contradictory signals. This ensures that a sensor signal that represents the state "incorrect positioning of the consumable means" and thus also can denote the absence of a consumable means does not lead to the withdrawal of a new consumable means from the magazine and therefore there is no unnecessary consumption of consumable means which thus prevents malfunctioning of the so-called continuous strip pile-up by this invention. The risk, of jamming of several analytical consumable means in the conveyance pathway (so-called strip jam) is thus largely eliminated by this design of the handheld analyzer with this functionality. This makes it possible to reduce the number of malfunctions due to the inventive design of the handheld analyzer.

In one embodiment, the handheld analyzer is configured to activate the analysis sensor for testing a sample for a medically significant component and then to trigger the analysis when correct positioning of an analytical consumable means in the conveyance pathway has been ascertained by means of a switch signal of the electric switch component which represents correct positioning of an analytical consumable means. This can be implemented independently of the optical sensor signal, which results in a very simple and robust implementation of the handheld analyzer and the method for operating the handheld analyzer. The electric switch component is prioritized herewith to a certain extent with respect to the optical sensor unit and the optical sensor unit begins to operate effectively for checking and/or verifying the switch signal of the electric switch component only when the switch signal of the electric switch component indicates that there is no analytical consumable means in the correct position on the conveyance pathway.

The present invention also relates to a method for operating a handheld analyzer for testing a sample, in particular a biological fluid, for a medically significant component, wherein the handheld analyzer comprises a display device, a withdrawal device for withdrawing an analytical consumable means from a magazine, in particular a rotary drum magazine, and for conveying it onto a conveyance pathway, an analysis sensor to which an analytical consumable means can be supplied on the conveyance pathway, and a test unit which detects the correct positioning of an analytical consumable means in the conveyance pathway. The method also has the specific features, that after activation of the handheld analyzer and the subsequent withdrawal of an analytical consumable means from the magazine and conveying it onto the conveyance pathway, signals of an electric switch component which mechanically senses the positioning of an analytical consumable means on the conveyance pathway and of an optical sensor unit which optically senses the positioning of an analytical consumable means on the conveyance pathway are analyzed by a control unit, and the handheld analyzer is controlled as a function of the comparison of these signals.

Joint analysis of signals is performed by verifying and/or checking the respective positions detected, and as a function thereof in particular the analysis sensor and/or the withdrawal device and/or the display device are controlled. Through the inventive option of checking and/or verifying the various signals representing a positioning of the consumable means on the conveyance pathway, it is possible to reduce malfunctions and faulty operation that may be associated with malfunctions, which greatly improves the usability and reliability in use of the analyzer according to the invention.

In one embodiment, the handheld analyzer is configured to start or release the measurement operation by the analysis sensor independently of the optical sensor signal when the correct positioning of an analytical consumable means has been detected by the electric switch component. This design makes use of the fact that the switch signal of the electric switch component which represents positively a correct positioning is a very reliable signal which as a rule does not require checking and/or verification. Due to this design, a very simple and sufficiently reliable method of operating a handheld analyzer is provided.

In other embodiments, the method for operating the handheld analyzer is configured and arranged such that the withdrawal of an analytical consumable means by the withdrawal device is suppressed when the signal of either the electric switch component or the signal of the optical sensor unit represents the correct positioning while the respective other signal represents an incorrect positioning of an analytical consumable means so that the two signals contradict one another. In this case, the present invention ensures that the withdrawal of another new analytical consumable means from the magazine is prevented so that the unwanted malfunction of continuous conveyance of consumable means in the manner of a continuous strip pile-up and/or jamming of consumable means in the conveyance pathway in the manner of a strip jam is prevented. In addition, there can also be a specific error message carried out by use of the display device.

If incorrect positioning of the analytical consumable means is detected by the electric switch component as well as the optical, sensor unit, in particular if the absence of such an analytical consumable means is detected and thus mutually confirmed, then the withdrawal device is activated and thus a consumable means is withdrawn from the magazine and conveyed over the conveyance pathway in the direction of the analysis sensor where correct positioning of the consumable means is detected and checked with the help of the inventive test unit. By means of the inventive type of verification of the correct positioning of the consumable means on the conveyance pathway, very reliable operation of the handheld analyzer is ensured, this operation being characterized by a very low number of malfunctions.

The operating reliability can be further improved by checking on whether the magazine has been emptied completely and in this case preventing further activation of the withdrawal device if incorrect positioning is detected and the respective confirmation is obtained. With the help of the display device, an error message indicating that the magazine has been emptied completely is preferably output. By this embodiment of the inventive method, especially convenient handling of the analyzer is provided, largely ruling out faulty operation of the handheld analyzer or malfunction thereof.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figures 1, 2:
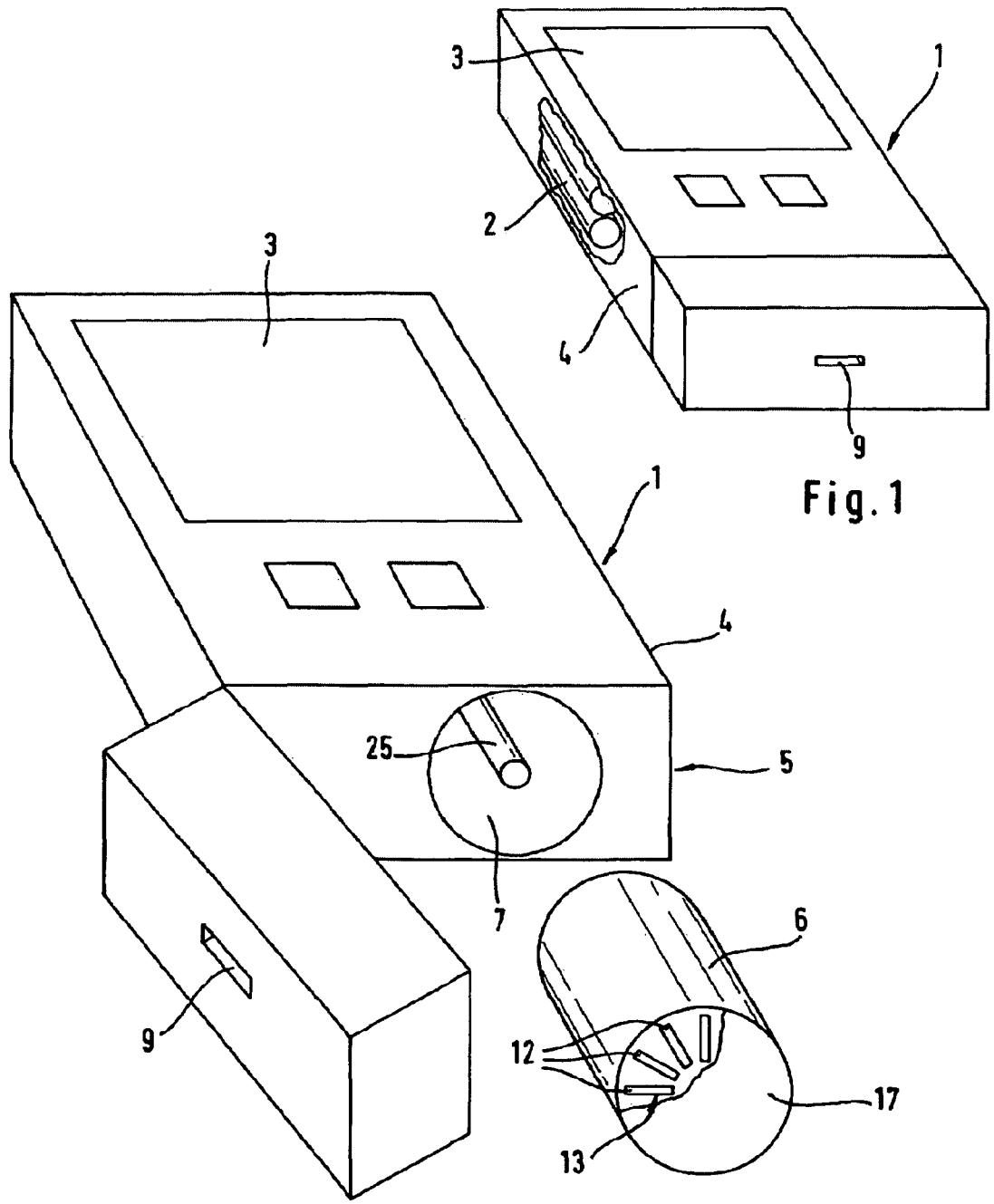
FIG. 1 shows an exemplary embodiment of a handheld analyzer.
FIG. 2 shows the handheld analyzer illustrated in FIG. 1 with the magazine compartment opened with the rotary drum magazine and the analytical consumable means.
Figure 3:
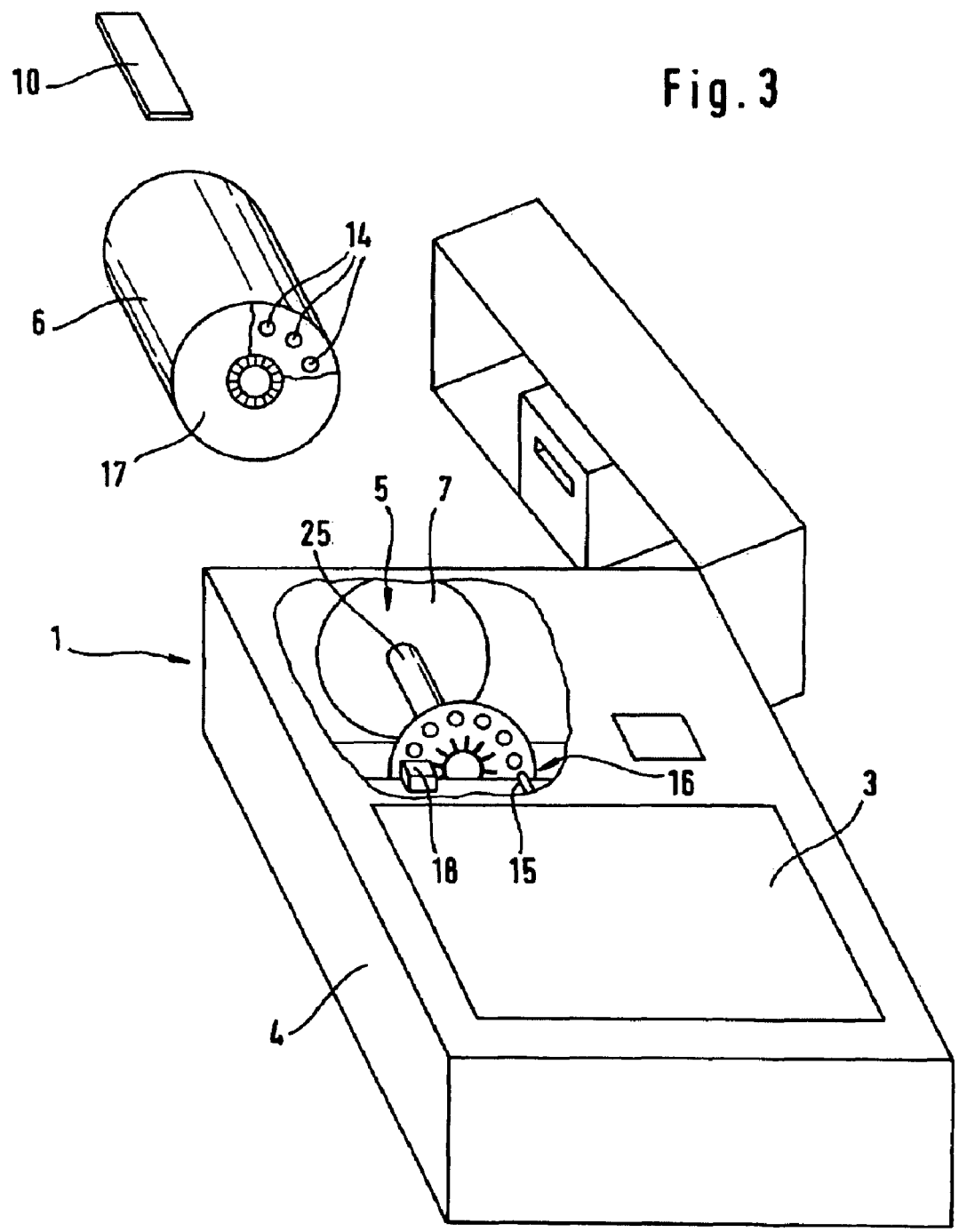
FIG. 3 shows another view of the handheld analyzer from FIG. 2.

FIGS. 1 through 3 show various views of a compact portable handheld analyzer 1 for testing a medically significant component of a sample, in particular a biological fluid such as blood, urine or saliva. The handheld analyzer 1 shown in FIG. 1 is used to determine the blood glucose level and has an integrated power supply 2 in the form of conventional batteries or solar cells. The result of an analysis is displayed with a display device 3, such as an energy-saving liquid crystal display or an OLED display. The handheld analyzer 1 has a housing 4, which has a loading opening 5 for receiving a replaceable rotary drum magazine 6 into a magazine compartment 7, where the rotary drum magazine 6 is incrementally rotatable about its geometric longitudinal axis by means of a drive. FIG. 1 shows the handheld analyzer 1 with the loading opening 5 closed. FIGS. 2 and 3 show the handheld-analyzer 1 with the loading opening 5 opened. FIG. 3 shows only a part of the housing 4 cut away to better illustrate the design, so that one can see into the magazine compartment 7.

In an end face, the housing 4 has an output opening 9 for analytical consumable means 10 stored in the rotary drum magazine 6. These consumable means 10 can be designed as test strips to which a sample can be applied. A reagent contained in the test strip reacts with a medically significant component of the sample so that the result of the reaction can be analyzed with an analysis device of the handheld analyzer 1. Such an analysis device may comprise, for example, an optical sensor as the analysis sensor which detects a color change in a consumable means 10 designed as a test strip or it may comprise a sensor which determines a change in conductivity of the sample.

The rotary drum magazine 6 has multiple chambers 12 arranged in a ring around its geometric longitudinal axis, which chambers may contain analytical consumable means 10. The chambers 12 can be positioned one after the other in a withdrawal position by incrementally rotating the rotary drum magazine 6, so the consumable means 10 can be withdrawn from the respective chamber 12 of the rotary drum magazine 6 as needed and can be output through the output opening 9 of the housing 4.

Any number of such chambers 12 may be selected. As a rule, 10 to 100 chambers 12 are expedient, but 15 to 30 chambers 12 are preferably provided. Each of the chambers 12 has a withdrawal opening 13 for withdrawing a consumable means 10 on an end face of the rotary drum magazine 6 and has an insertion opening 14 on the side opposite the withdrawal opening 13 for insertion of a push rod 15 of a withdrawal device 16. The insertion, openings 14 and the withdrawal openings 13 are closed with a sealing film 17 to protect the consumable means 10. As described in EP 1 022 565, consumable means 10 can be pushed out of the chambers 12 with the push rod 15 for use, puncturing the sealing film 17 of the insertion opening 14 by the push rod 15 and puncturing the sealing film 17 of the withdrawal opening 13 by the consumable means 10.

With the help of the rotary drum testing device 8, a signal is generated, containing information about whether one of the insertion openings 14 is sealed with a sealing film 17 and thus a consumable means 10 intended for use is contained therein. By means of the rotary drum testing device 18, it is possible to check whether the rotary drum magazine 6 is completely emptied. As an alternative or in addition to the rotary drum testing device 18, a counting device may also be provided, to count the number of consumable means withdrawn from the chambers 12 of a rotary drum magazine 6 and to output a "rotary drum empty" signal on reaching the maximum number.

Figure 4:
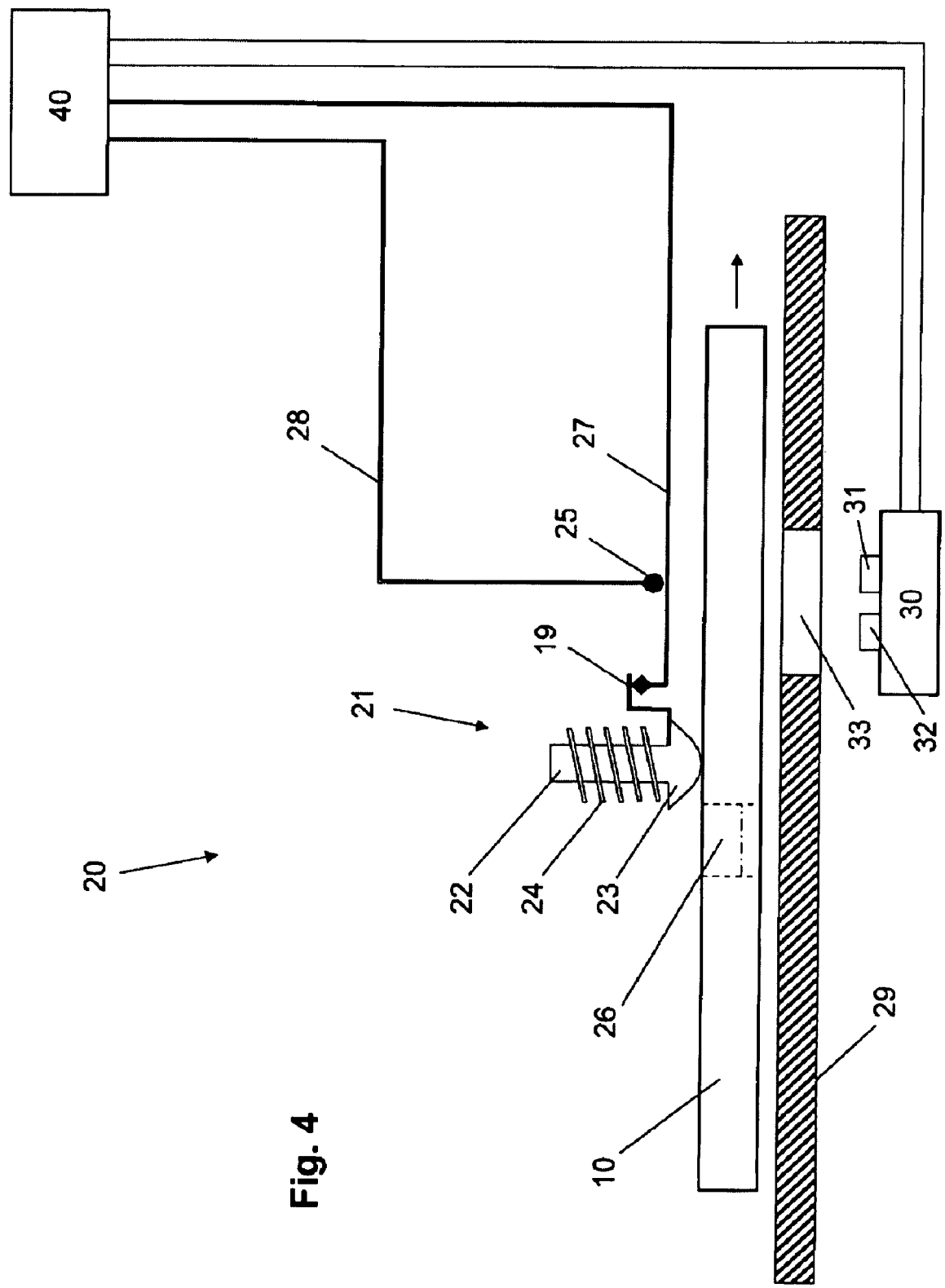
FIG. 4 shows a detail of an exemplary embodiment of a handheld analyzer with an electric switch component and an optical sensor unit.

FIG. 4 shows a schematic diagram of a design of the test unit 20 which detects the correct positioning of an analytical consumable means 10 in the conveyance pathway and, in doing so, additionally supports the correct positioning and/or preserves the correct positioning as a positioning device.

The test unit 20 essentially comprises the control unit 40 and the optical sensor unit 30 as well as the electric switch component 21. The optical sensor unit 30 and the electric switch component 21 both have the function of sensing the positioning of an analytical consumable means 10 on the conveyance pathway and delivering a switch signal that represents the positioning and/or delivering a corresponding sensor signal to the control unit 40 to be able to control the handheld analyzer 1 and/or individual components thereof on the basis of a common analysis of these signals.

In one embodiment, the electric switch component 21 has a peg 22, which is typically designed to be displaceable and has an end 23 tapering conically in the direction of the analytical consumable means 10 and assigned to the analytical consumable means 10. The conically tapering end 23 of the peg 22 is designed so that it can engage in a recess 26 of the analytical consumable means 10 in the measuring position of the consumable means 10 and can position it because of the conical taper of the end 23. Due to this positioning in the sense of securing a position, a reliable optical analysis of the consumable means 10 by means of the analysis sensor of the handheld analyzer 1, which is also implemented by the optical sensor unit 30, for example, is ensured. Reliable optical detection of the correct positioning of the consumable means 10 with the help of the optical sensor unit 30 may thus also be ensured. The recess 26 may also be designed as a hole penetrating through the consumable means 10. This is indicated by a dash-dot bar in the recess 26 in FIG. 4. Other advantageous embodiments of electric switch components 21 are described in the document EP 1 508 807.

FIG. 4, however, shows the consumable means 10 not arranged in the measurement position in the conveyance pathway in which the analysis is performed. Consequently, the conically tapering end 23 of the peg 22 also has not penetrated into the recess 26 and/or the hole in the consumable means 10 and it sits on the surface of the consumable means 10. The consumable means 10 has been conveyed into the conveyance pathway in the direction of the arrow up to the position as illustrated in which its correct positioning in the conveyance pathway is verified by the test unit 20. In this verification, a check is performed to ascertain whether a consumable means 10 is situated in the test position in the conveyance pathway, i.e., it has arrived in this test position so to speak from a chamber of the rotary drum magazine through the conveyance by means of the withdrawal device. After testing the correct positioning of the consumable means 10 (in the test position illustrated), it is conveyed further in the direction of the arrow until reaching the measurement position in which the end 23 penetrates into the recess 26 and the analysis is performed.

As shown, the consumable means 10 can be arranged in the conveyance pathway in the area of the electric switch component 21 and/or in the area of the optical sensor unit 30 on a supporting surface 29. By introducing the analytical consumable means 10, the peg 22 is displaced upward out of the resting position, which is defined by contact of the end 23 with the supporting surface 29, into the position shown here, in which it rests on the top side of the consumable means 10. This displacement is induced by the advance of the consumable means 10 in the direction of the arrow and by sliding along the outflow edge of the conically tapering end 23. This displacement of the peg 22 perpendicular to the conveyance pathway and/or to the supporting surface 29 is accomplished against a spring force which is generated by the spring 24. The spring 24 ensures that the peg 22 is held in the resting position until the consumable means 10 displaces it against the spring force into a displaced position, e.g., into the position shown here.

Depending on the displacement of the peg 22, an electric contact 25 is closed or opened by means of the peg 22 and a mechanical contact 19 between the peg 22 and a contact spring 27. The two contacts of this electric contact 25 are implemented by the movable contact spring 27 and the fixed spring plate 28. In the situation depicted here, the peg 22 allows contact between the contact spring 27 and the spring plate 28 to close the electric contact 25, thereby generating an electric signal which indicates the correct positioning (the presence) of a consumable means 10. In the resting position of the peg 22, i.e., in the absence of consumable means 10, the electric contact 25 between the contact spring 27 and the spring plate 28 is opened due to the mechanical contact 19 which presses the contact spring 27 downward, thereby signaling that no consumable means is present. On insertion of the consumable means 10 into the conveyance pathway, the contact spring 27 is thus deflected in the direction of the spring plate 28 and closes the electric contact 25, so that the control unit 40 receives an electric switch signal representing the state of correct positioning of the consumable means 10. The electric contact 25, consisting of the contact spring 27 and the spring plate 28, is closed.

If there is no analytical consumable means 10 in the conveyance pathway, then the peg 22 is shifted by the spring 24 into the resting position where it is in contact with the supporting surface 29 and thus no longer presses the contact spring 27 against the spring plate 28. The electric contact 25 is opened and no electric switch signal is transmitted to the control unit 40. This represents the switch information that no analytical consumable means 10 is present in the monitoring area of the electric switch component 21.

In this switch state, the electric contact 25 is opened. The handheld analyzer 1 is usually in this switch state whenever it is not being used and when it is being transported by the user. Especially when being transported in a pocket or in one's clothing, there is the risk that dirt particles might penetrate through openings in the housing 4 of the handheld analyzer 1 and remain in the interior of the housing 4. Dirt particles which come to lie in the area of the electric contact 25 of the electric switch component 21 and thereby prevent electric contact between the contract spring 27 and the spring plate 28 are especially harmful. In this case, the presence of an analytical consumable means 10 leads to deflection of the peg 22 but this cannot result in contact because that is prevented by dirt particles. For lack of electric contact, the control unit 40 cannot receive any information about the correct positioning and/or presence of the analytical consumable means 10. The mechanical movement of the peg 22 or of the mechanical contact 19 may also be hindered by dirt particles.

The electric switch component 21 is designed as an active optical sensor unit 30 comprising an LED 31, which emits light of a limited frequency range in the direction of the consumable means 10. In an embodiment not depicted in FIG. 4, the optical sensor unit 30 may be arranged on the side of the consumable means 10 opposite the side facing the supporting surface 29. In FIG. 4, the optical sensor unit 30 would then be arranged above the consumable means 10, i.e., on the same side as the electric switch component 21, next to and directly adjacent to the latter. The area of the supporting surface 29 facing the optical sensor unit 30 could then be designed to be black in the area of the optical sensor unit 30. In this way only a small amount of light is backscattered from the supporting surface 29. If a consumable means 10 is situated in the area exposed to the light of the optical sensor unit 30, the consumable means typically having a light surface, in particular a white surface, e.g., a white field (so-called white level adjustment) which is used as part of the analysis for calibration purposes, then the amount of reflected light is greatly increased. The reflected light is detected by a photosensor 32 of the optical sensor unit 30. These two states differ greatly in the extent of the reflected light and the light received by the photosensor 32 so that these two states can be differentiated very reliably by means of the optical sensor unit 30. The latter sends a corresponding sensor signal to the control unit 40, representing either the state of correct positioning of the consumable means 10 in the conveyance pathway and thus on the supporting surface 29 or representing the state in which no consumable means 10 is present in the conveyance pathway. The control unit 40 analyzes the two signals of the electric switch component 21 and the optical sensor unit 30 jointly, resulting in a check and/or verification of the electric switch signal with the help of the sensor signal.

In the embodiment shown in FIG. 4, the optical sensor unit 30 is arranged on the side of the consumable means 10 which is facing the supporting surface 29. The optical sensor unit 30 is thus situated beneath the consumable means 10, i.e., on the side of the consumable means 10 which is opposite the electric switch component 21. The supporting surface 29 for this reason has, an opening or a transparent window area 33 in the area of the optical sensor unit 30. If there is no consumable means 10 in the area exposed to the radiation of the optical sensor unit 30, then only a small amount of scattered light is scattered back to the photosensor 32. However, if there is a consumable means 10, which typically has a light surface, in particular a white surface, in the area exposed to the radiation from the optical sensor unit 30, e.g., a white field (so-called white level adjustment), which is used for calibration purposes as part of the analysis, the amount of reflected light is greatly increased. The reflected light is detected by a photosensor 32 of the optical sensor unit 30. These two states differ greatly in the extent of the reflected light and the light received by the photosensor 32 so that these two states can be differentiated very reliably by means of the optical sensor unit 30. The sensor unit delivers a corresponding sensor signal to the control unit 40, representing either the state of correct positioning of the consumable means 10 in the conveyance pathway and thus on the supporting surface 29 or representing the state in which no consumable means 10 is present in the conveyance pathway. The control unit 40 analyzes the two signals of the electric switch component 21 and the optical sensor unit 30 jointly, so there is a check and/or verification of the electric switch signal with the help of the sensor signal.

For both embodiments described in the context of FIG. 4, the remaining measurement process is carried out after verifying the correct positioning of a consumable means 10 in the position of the consumable means 10 illustrated in FIG. 4. In this measurement process in some embodiments the analysis may be performed using an analysis sensor directly in this position of the consumable means 10. However, if the optical sensor unit 30 serves at the same time as an analysis sensor or if the analysis sensor is integrated into the optical sensor unit 30, then it is usually necessary to convey the consumable means 10 further out of the position illustrated here into the measurement position in the direction of the arrow until, for example, a photometrically measured test field appears in the visible area of the analysis sensor. In the measurement position of the consumable means 10, the end 23 of the peg 22 can then penetrate into the recess 26. Then either the electric contact 25 can remain closed and thus the correct positioning, i.e., the presence of a consumable means 10 may be signaled further. However, in preferred embodiments, the electric contact 25 opens in the measurement position of the consumable means 10 to thereby provide a signal indicating that the consumable means 10 has reached the measurement position. The fact that the opened electric contact 25 then seemingly indicates that no consumable means 10 is present can be taken into account by a corresponding sequence control by means of the control unit 40 in which the correct positioning of the consumable material 10 in the measurement position has previously been verified.

Figure 5:
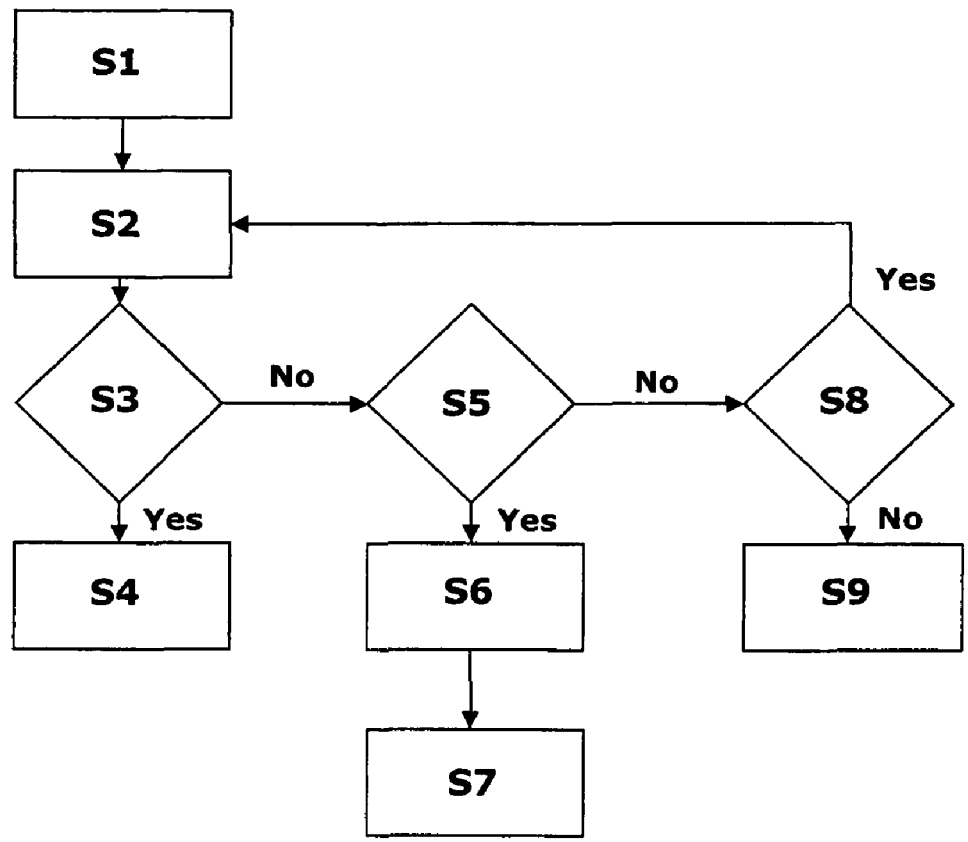
FIG. 5 shows a diagram of an exemplary method for operating a handheld analyzer.

FIG. 5 shows schematically the verification and/or control of the handheld analyzer with special attention to the function of the test unit 20 in the form of a flow chart as an example.

After the handheld analyzer 1 has been activated in step S1 by operation of a button and thus an analytical consumable means 10 designed as a test strip has been requested, in step S2, a strip-shaped consumable means 10 is withdrawn from the rotary drum magazine 6 by means of the withdrawal device 16 and is conveyed onto the conveyance pathway and conveyed thereon in the direction of the analysis sensor. The strip-shaped consumable means 10 then reaches the area of the electric switch component 21 and/or of the optical sensor unit 30. The peg 22 of the electric switch component 21 is shifted by the strip-shaped consumable means 10 and then closes the electric contact between the spring plate 28 and the contact spring 27. Thus the switch signal representing the state of correct positioning of the consumable means 10 is provided to the control unit 40. This detection takes place in step S3. If the switch signal for correct positioning of the consumable means 10 is delivered to the control unit 40 by the electric switch component 21, then according to step S4 the analysis sensor is activated and the analysis of the sample to be analyzed for a medically significant component such as glucose is performed. The measurement result is then output by the display device 3. This measurement sequence makes use of the fact that the reliability of detection of the electric switch component 21 for the state of correct positioning of the consumable means 10 is very high and therefore the measurement process can be started by the analysis sensor in a simple and direct manner.

If according to step S3, the electric switch component 21 detects the state of no correct positioning of the consumable means 10 and sends this information to the control unit 40, then an optical detection of correct positioning is performed subsequently by the optical sensor unit 30. This is done in step S5. The optical sensor unit 30 is activated exclusively in this case; otherwise it is deactivated. The optical sensor unit 30 is thus activated for checking and/or verifying the switch signal of the electric switch component 21 only when the switch signal of the electric switch component 21 indicates that there is no analytical consumable means 10 in the correct position on the conveyance pathway. Therefore, a very energy-saving operation of the handheld analyzer 1 is made possible. The optical sensor unit 30 is advantageously activated automatically for checking and/or verifying the switch signal of the electric switch component 21 when the withdrawal device 16 has been activated for conveying an analytical consumable means 10 onto the conveyance pathway but the switch signal of the electric switch component 21 indicates that no analytical consumable means 10 is in the correct position on the conveyance pathway.

If it is now found in step S5 that no consumable means 10 is in the detection range of the optical sensor unit 30, then this corresponds to a confirmation of the electric switch signal, whereupon the control unit 40 activates the withdrawal device 16 to withdraw the next consumable means 10 from the next chamber of the rotary drum magazine 6 and to convey it in the direction of the analysis sensor. This ensures that according to the request according to step S1, a consumable means 10 is conveyed to perform the desired analysis. If it is found by the rotary drum testing device 18 or a counting device according to step S8 that the rotary drum has been emptied completely and therefore no consumable means 10 is now present in the rotary drum magazine 6, then this is reported to the user with the help of the display device 3 according to step S9 and further operation of the handheld analyzer 1 is stopped.

If correct positioning and thus the presence of the consumable means 10 according to step S5 is detected by the optical sensor unit 30 and a corresponding sensor signal is provided to the control unit 40, then the contradictory signal content is detected by the control unit 40 and interpreted as a malfunction of the handheld analyzer 1. This malfunction is characterized in that to a strip-shaped consumable means 10 is present in the area of the electric switch component 21 and in the area of the optical sensor 30 but is not detected by the electrical switch component 21 and therefore the measurement operation is not started according to step S4. In this case, according to step S6, an error message is output by means of the display device 3, pointing out this malfunction and instructing the user to perform a cleaning of the electric contacts 27, 28 of 15 the switch component 21. This may be done automatically by starting a corresponding cleaning program of the handheld analyzer 1. Therefore the functionality of the electric switch component 21 is restored and thus the functionality of the handheld analyzer 1 is restored.

In addition to the output of the error message, according to step S7 the consumable means 10 is pushed out of the device and therefore the possibility of performing a successful analysis in the future after a successful cleaning is also provided.

In step S5, there is thus an analysis of the switch signal of the electric switch component 21 and the sensor signal of the optical sensor unit 30 and the handheld analyzer 1 is controlled as a function of the comparison of these signals by the control unit 40. The operating sequence described here ensures that it is possible to largely prevent the malfunctions of the so-called continuous strip pile-up in which consumable means 10 are continuously conveyed out of the rotary drum magazine 6 with the help of the withdrawal device 16 without resulting in an analysis and/or the malfunction of a strip jam in which another consumable means 10 is pushed onto a consumable means 10, which is already present in the conveyance pathway, leading to jamming of the consumable means 10 in the conveyance pathway.

The method steps described above can be characterized briefly as follows: S1 activation of the handheld analyzer, S2 test strip withdrawal, S3 switch signal query, S4 activation of analysis, S5 sensor signal query, S6 error message, S7 test strip output, S8 check on magazine supply and S9 magazine empty.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, to essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A handheld analyzer for testing a biological fluid for a medically significant component, comprising a display device, a housing, a loading opening for receiving a replaceable magazine containing a plurality of analytical consumable means, a withdrawal device for withdrawing one of the analytical consumable means from the magazine and for conveying it onto a conveyance pathway, an analysis sensor to which an analytical consumable means may be supplied on the conveyance pathway, and a test unit which detects the correct positioning of an analytical consumable means in the conveyance pathway, wherein the test unit comprises an electric switch component configured for mechanically sensing the positioning of an analytical consumable means on the conveyance pathway, assuming at least one position which represents the presence of an analytical consumable means and delivering a switch signal as a function of the positioning of the analytical consumable means, the test unit further comprising an optical sensor unit configured for optically sensing the positioning of an analytical consumable means on the conveyance pathway and delivering a sensor signal as a function of the positioning of the analytical consumable means, and the test unit further comprising a control unit configured for analyzing the switch signal of the electric switch component, analyzing the sensor signal of the optical sensor unit, and controlling the handheld analyzer as a function of the comparison of these signals.

2. The handheld analyzer according to claim 1, wherein the replaceable magazine comprises a rotary drum magazine, and wherein the plurality of analytical consumable means comprise a plurality of test strips.

3. The handheld analyzer according to claim 1, wherein the electric switch component comprises a displaceable peg as a switch element with a conically tapering end facing the analytical consumable means, and wherein each of the analytical consumable means comprises at least one of an elevation or recess corresponding to the conically tapering end of the peg as a position-specific surface design.

4. The handheld analyzer according to claim 3, wherein the displaceable peg is spring-mounted.

5. The handheld analyzer according to claim 3, wherein the position-specific surface design comprises a contour configured to influence the deflection of the peg depending on the position of the analytical consumable means in the conveyance pathway, the contour being selected from the group consisting of a channel that varies with at least one of width or depth, and a ramp that varies with at least one of width or height.

6. The handheld analyzer according to claim 1 wherein the electric switch component comprises a switch element and the optical sensor unit is configured for determining the position of the switch element.

7. The handheld analyzer according to claim 6 wherein the switch element comprises a displaceable peg.

8. The handheld analyzer according to claim 1, wherein the optical sensor unit is configured for determining one of the presence or position of the analytical consumable means on the basis of its reflective or transmitting optical properties.

9. The handheld analyzer according to claim 1, wherein the optical sensor unit forms a joint sensor unit together with the analysis sensor.

10. The handheld analyzer according to claim 1, wherein the withdrawal of an analytical consumable means from the magazine by the withdrawal device is prevented by the control unit when either the switch signal of the electric switch component or the sensor signal of the optical sensor unit represents the correct positioning and the respective other signal represents the incorrect positioning of an analytical consumable means on the conveyance pathway.

11. The handheld analyzer according to claim 10 wherein an error message is output on the display device when the withdrawal of an analytical consumable means is prevented by the control unit.

12. The handheld analyzer according to claim 1, wherein the analysis sensor is configured to be activated to test a sample for a medically significant component when the correct positioning of an analytical consumable means in the conveyance pathway has been detected by means of a switch signal of the electric switch component which represents the correct positioning of an analytical consumable means.

13. The handheld analyzer according to claim 1, wherein the optical sensor unit is configured to be activated for at least one of checking or verifying the switch signal of the electric switch component only when the switch signal of the electric switch component indicates that there is no analytical consumable means in the correct position on the conveyance pathway.

14. A method for operating a handheld analyzer for testing a biological fluid for a medically significant component, the method comprising the steps of:
selecting the handheld analyzer comprising a display device, a withdrawal device, for withdrawing an analytical consumable means from a magazine and for conveying said means onto a conveyance pathway, an analysis sensor to which the analytical consumable means can be supplied on the conveyance pathway, and a test unit comprising an electric switch component, an optical sensor unit and a control unit, the test unit being configured to detect the correct positioning of an analytical consumable means in the conveyance pathway;
activating the handheld analyzer;
withdrawing, one of the analytical consumable means from the magazine and conveying said means onto the conveyance pathway;
analyzing a switch signal from the electric switch component using the control unit, the electric switch component being configured for mechanically sensing the positioning of an analytical consumable means on the conveyance pathway;
analyzing a sensor signal from the optical sensor unit using the control unit, the optical sensor unit being configured for optically sensing the positioning of the analytical consumable means on the conveyance pathway; and
controlling the handheld analyzer as a function of the comparison of the switch signal and the sensor signal.

15. The method for operating a handheld analyzer according to claim 14, further comprising the step of releasing the analysis sensor for performing a measurement operation for testing the sample for a medically significant component when correct positioning by the electric switch component has been signaled.

16. The method for operating a handheld analyzer according to claim 14, further comprising the step of activating the optical sensor unit for at least one of checking or verifying the switch signal only when the switch signal indicates that there is no analytical consumable means in the correct position on the conveyance pathway.

17. The method for operating a handheld analyzer according to claim 14, further comprising the step of activating the optical sensor unit for at least one of checking or verifying the switch signal when the withdrawal device has been activated but the switch signal indicates that there is no analytical consumable means in the correct position on the conveyance pathway.

18. The method for operating a handheld analyzer according to claim 14, further comprising the steps of suppressing the withdrawal of an analytical consumable means by the withdrawal device when one of the switch signal or the sensor signal represents the correct positioning of the analytical consumable means and the other respective signal indicates incorrect positioning of the analytical consumable means, and outputting an error message on the display device.

19. The method for operating a handheld analyzer according to claim 14, further comprising the step of activating the withdrawal device when the electric switch component detects that the positioning of the analytical consumable means is not correct and the incorrect positioning is confirmed by the optical sensor unit.

20. The method for operating a handheld analyzer according to claim 19, further comprising the steps of preventing further activation of the withdrawal device when complete emptying of the magazine has been detected, and outputting an error message on the display device.

* * * * *